US010314738B1

(12) United States Patent
Gelfand et al.

(10) Patent No.: US 10,314,738 B1
(45) Date of Patent: Jun. 11, 2019

(54) THERMAL THERAPEUTIC APPARATUS

(71) Applicant: Lightbulb, LLC, Franklin, TN (US)

(72) Inventors: Matt Gelfand, Franklin, TN (US); Rich Crim, Franklin, TN (US); Chuck Flueck, Franklin, TN (US)

(73) Assignee: Lightbulb, LLC, Franklin, TN (US)

( * ) Notice: Subject to any disclaimer, the term of this patent is extended or adjusted under 35 U.S.C. 154(b) by 742 days.

(21) Appl. No.: 14/525,514

(22) Filed: Oct. 28, 2014

Related U.S. Application Data

(60) Provisional application No. 61/896,588, filed on Oct. 28, 2013.

(51) Int. Cl.
*A61H 15/02* (2006.01)
*A61F 7/00* (2006.01)
*A61F 7/02* (2006.01)
*A61F 7/03* (2006.01)

(52) U.S. Cl.
CPC ............... *A61F 7/03* (2013.01); *A61H 15/02* (2013.01); *A61F 2007/0087* (2013.01); *A61F 2007/0088* (2013.01); *A61F 2007/0279* (2013.01)

(58) Field of Classification Search
CPC ........................................................ A61N 15/02
See application file for complete search history.

(56) References Cited

U.S. PATENT DOCUMENTS 4,668,564 A * 5/1987 Orchard .................... A61F 7/02 264/46.4
5,545,456 A * 8/1996 Suida ..................... A47K 7/022 15/208
6,007,501 A * 12/1999 Cabados ................ A61H 39/04 601/131
6,024,762 A * 2/2000 Gray .................... A47G 9/1036 5/636
7,156,817 B1 * 1/2007 Cassidy Phillips .......................... A61H 15/0092 601/131
8,156,939 B1 * 4/2012 Maddalena ........ A61H 15/0092 128/845
2003/0144616 A1 * 7/2003 Henderson ............. A61H 15/00 601/131
2003/0176264 A1 * 9/2003 Burns ................... A61H 11/00 482/148
2005/0015032 A1 * 1/2005 Stein ...................... A61H 15/02 601/131
2007/0106356 A1 * 5/2007 Carstens .............. A41D 13/005 607/112
2012/0265108 A1 * 10/2012 Young ........................ A61F 7/03 601/15
2013/0085426 A1 * 4/2013 Brodsky ................ A61H 15/00 601/128
2014/0024984 A1 * 1/2014 Allen ...................... A61H 7/007 601/134

* cited by examiner

*Primary Examiner* — Kaitlyn E Smith
(74) *Attorney, Agent, or Firm* — Patterson Intellectual Property Law, P.C.; Ryan D. Levy

(57) ABSTRACT

A thermal therapeutic apparatus is provided which includes a resilient shell, a thermal exchange material, and a flexible sleeve. The resilient shell includes an outer surface and inner cavity in which the thermal exchange material is disposed. The flexible sleeve at least partially covers the shell and defines a vent region which permits communication of air and through the sleeve.

10 Claims, 12 Drawing Sheets

THERMAL THERAPEUTIC APPARATUS

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application claims benefit of the following patent application(s) which is/are hereby incorporated by reference in their entirety: 61/896,588.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to therapeutic devices or apparatuses that may be used for massage therapy. More particularly, this invention pertains to thermal apparatuses that may be warmed or cooled and used to massage an individual. The invention may also include multiple formations for providing different therapeutic benefits in administering or absorbing heat.

Individuals commonly engage in different types of physical therapy to alleviate pain and discomfort associated with tight muscles. In doing so, physical therapists often are engaged to perform procedures on an individual to relax contracted muscles or otherwise reduce knots in a patient's body. After performing such procedures the physical therapist usually provides instructions on how to maintain muscle fibers in a relaxed state through self-administered massage therapy by the user at home.

There are common commercial electronic massagers on the market which can include vibrating or other mechanical movements that may be used with massage therapy to alleviate muscle pain. Most of these are relatively expensive and require DC or AC current to operate. Alternatives to such devices include non-electrical massage devices of a variety of shapes and sizes. Some individuals utilize recreational sporting balls such as tennis balls or lacrosse balls to administer massage therapy to themselves. For example, an individual may utilize a tennis ball within a sock to administer massage therapy to either the user's neck or back. In doing so, a user may stand up against a wall with a tennis ball within a sock between the user's back and the wall to massage different parts of the back. While this device can provide some type of massage therapy, there is much lacking in its design.

What is needed, then, is a thermal therapeutic device that can administer or absorb heat while providing massage therapy to a user. In addition, it is desired to have a specific resistance or rigidity so that the therapeutic device provides sufficient force and resistance in massaging a user's body.

BRIEF SUMMARY OF THE INVENTION

Aspects of the present invention provide a thermal therapeutic apparatus including a resilient shell, a thermal exchange material, and a flexible sleeve. The resilient shell includes an outer surface and inner cavity which holds the thermal exchange material. The flexible sleeve at least partially covers the shell and defines a vent region which permits communication of air and moisture from the shell through the sleeve.

In one aspect of the invention, a permeable plug spans the aperture. The permeability of the plug is sufficient to permit air and moisture through the aperture while also preventing passage of the thermal exchange material from the inner cavity.

In another aspect of the invention, a plurality of resilient shells are provided, each of which is at least partially covered by the sleeve. An aperture of a first shell is directed toward a first side of the sleeve while an aperture of a second shell is directed toward a second side of the sleeve.

Other aspects of the invention provide a flexible sleeve, resilient shell, and permeable plug. The flexible sleeve includes an interior and exterior face. A vent hole extends from the interior face to the exterior face. The resilient shell may be disposed within the sleeve and includes an inner cavity, outer surface, and aperture. The aperture extends between the inner cavity and outer surface, and also allows a thermal exchange material to be inserted into the inner cavity. The permeable plug is disposable within aperture and configured to prevent the thermal material from passing through the aperture while permitting communication of air and moisture through the aperture.

Still other aspects of the invention provide a flexible sleeve which includes an inner cavity, an outer surface, and an aperture therethrough. A thermal exchange material is disposed within the shell while a sleeve is disposed at least partially about the shell outer surface. The sleeve defines a vent hole that is positioned over the aperture, and a vent membrane is disposed across a portion of the vent hole. The vent membrane has a sufficient vent permeability to permit the passage of air and moisture.

DETAILED DESCRIPTION OF THE INVENTION

Figure 1:
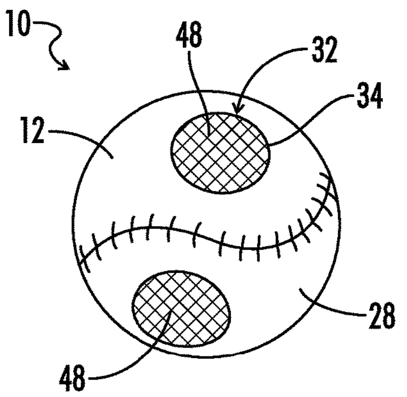
FIG. 1 is a perspective view of one thermal therapeutic apparatus embodiment.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims. The phrase "in one embodiment," as used herein does not necessarily refer to the same embodiment, although it may.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states.

The term "when" is used to specify orientation for relative positions of components, not as a temporal limitation of the claims or apparatus described and claimed herein unless otherwise specified.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or multiple components. Similarly, to the extent the term "attach" is used in the specification or claims, it is intended to mean not only "directly attached to," but also "indirectly attached to," such as attached through another component or multiple components.

Where the various figures may describe embodiments sharing various common elements and features with other embodiments, similar elements and features are given the same reference numerals and redundant description thereof may be omitted below. In the drawings, not all reference numbers are included in each drawing for the sake of clarity. In addition, positional terms such as "upper," "lower," "side," "top," "bottom," etc. refer to the apparatus when in the orientation shown in the drawing, unless otherwise noted.

Referring now to FIG. 1-4, a thermal therapeutic apparatus 10 is provided. As shown, the apparatus 10 includes a flexible sleeve 12 which at least partially covers a resilient shell 14. A thermal exchange material 16 is placed within the shell and emits or absorbs heat as needed by a user. The apparatus 10 provides an overall resilient structure that may be utilized for massaging a user's back, neck, or other anatomical areas. Before use, the apparatus 10 may be inserted within an oven, microwave, or otherwise high heat area to absorb heat energy which is later released during massaging uses. Alternatively, the apparatus 10 may be placed with a refrigerator, freezer, or otherwise low heat area until the temperature of the apparatus is substantially reduced. During subsequent uses, the apparatus 10 will provide a cooling experience as it absorbs heat emitted from a user.

The resilient shell 14 includes a concave structure which forms an inner cavity 18 defined by an inner cavity surface 19. The shell 14 receives and encloses the thermal exchange material 16. As a result, the apparatus 10 may act as a heat source or heat sink while the shell 14 is rolled and deformed during use. Opposite the inner cavity surface 19 is an outer surface 20 of the shell. In some embodiments, the outer surface 20 directly engages the sleeve 12 and forms a tight fit with respect to the shell 14. In such embodiments, the sleeve 12 is maintained in a substantially fixed position with respect to the shell 14.

The shell 14 may assume a variety of shapes and sizes. As shown in FIG. 1-4, the shell 14 of some embodiments is shaped as a sphere. As used herein, the term "sphere" or "ball" may be used interchangeably and may refer to a circular shaped device or a generally round device which may also have an oval or egg shaped exterior. The sphere of some embodiments will have a radius between approximately 1-20 centimeters. The sphere of certain embodiments will have a radius between approximately 2-10 centimeters. The sphere of other embodiments will have a radius between approximately 3-5 centimeters. It is also understood that optional embodiments of the apparatus 10 may be formed as different three-dimensional shapes (e.g., a prism, pyramid, cylinder, cone, or other irregular body) without departing from the invention as disclosed.

In some embodiments, the shell 14 defines an aperture 22 extending from the inner cavity 18 to the outer surface 20 along an aperture axis 23. This creates a void through the shell wall 24. The aperture 22 permits communication from the inner cavity 18 to an area outside the shell 14. If steam or moisture is emitted by thermal exchange material 16, it will pass through the aperture 22, allowing pressure to equalize within the inner cavity 18. Optionally, the aperture 22 also provides an access channel for insertion of the thermal exchange material 16. In such embodiments, the thermal exchange material 16 is added or inserted into the inner cavity 18 by first passing through the aperture 22 from an area outside the shell 14. A permeable plug 26 is optionally placed within or over the aperture 22. While the permeable plug 26 covers the aperture 22, unwanted insertion or removal of the thermal exchange material 16 is prevented.

Figure 6A:
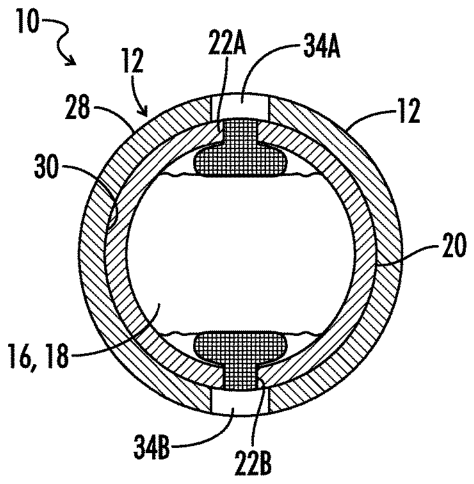
FIG. 6A is a cut-away view along axis A-A of another thermal therapeutic apparatus embodiment having a plurality of apertures.
Figure 6B:
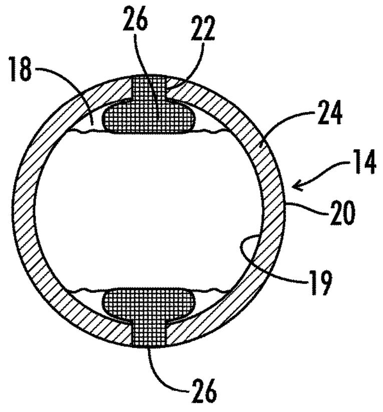
FIG. 6B is a cut-away view of the shell embodiment of FIG. 6A.

As shown in FIGS. 6A and 6B, certain embodiments of the apparatus 10 include a plurality of apertures 22 defined within the shell wall 24. In such embodiments, steam or other gases may be quickly and evenly dispersed from the inner cavity 18. In optional embodiments, the apertures 22 are defined at opposite ends of the shell 14. As used herein, "moisture" may refer to steam, water vapor and/or mist. During use, air or moisture within the shell 14 may pass from a first aperture 22A as ambient air passes through a second aperture 22B to the inner cavity 18. The apertures 22 may further be configured to provide a desired rate of heat exchange. Some, or all, of the apertures 22 may be filled or covered by a discrete permeable plug 26. In optional embodiments, no apertures 22 receive a permeable plug 26. Moisture or air may pass through the permeable plug.

The shell 14 may include, one or more resilient polymer materials. The resilient and elastic properties of the shell material allow it deform under the compressive forces generated during use. Similarly, those elastic properties allow the shell 14 to return to its original shape after the compressive forces are removed. In some embodiments, the shell 14 includes a natural rubber, synthetic rubber, or synthetic plastic material. Certain embodiments of the shell 14 include a rubber material and a shell wall thickness between approximately 0.5-30 millimeters. Select embodiments of the shell 14 include a rubber material rubber material and a shell wall thickness between approximately 1-10 millimeters.

As noted above, the thermal exchange material 16 is configured to fill at least a portion of the inner cavity 18. In some embodiments, the entirety of the inner cavity 18 is substantially filled by the thermal exchange material 16 disposed therein. The thermal conductivity of the thermal exchange material 16 is sufficient to slowly release or absorb heat energy applied thereto. The thermal exchange material 16 disposed within the inner cavity 18 may therefore act as a heat source or relatively cold heat absorber, depending on the desired use. In some embodiments, the thermal exchange material's thermal conductivity is between approximately 0.01-10 W/m·K. In other embodiments, the thermal conductivity of the thermal exchange material 16 is between approximately 0.05-5 W/m·K. In still other embodiments, the thermal conductivity of the thermal exchange material 16 is between approximately 0.10-1.5 W/m·K.

Figure 5A:
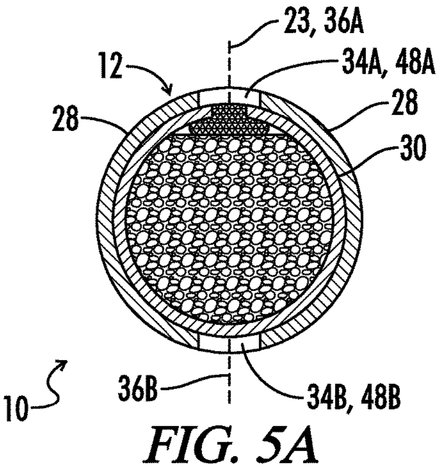
FIG. 5A is a cut-away view along axis A-A of a thermal therapeutic apparatus embodiment having a single aperture.
Figure 5B:
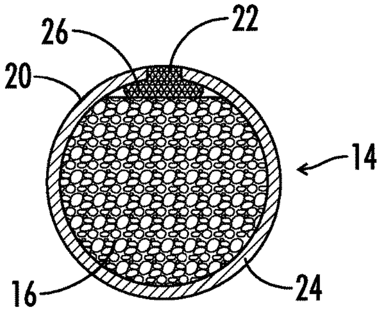
FIG. 5B is a cut-away view of the shell embodiment of FIG. 5A.

As seen in FIG. 5A-5B, some embodiments of the thermal exchange material 16 include a granular filler material which provides a desired thermal conductivity and resistance to deformation. In certain embodiments, the granular filler includes an organic material. Select embodiments of organic material include flaxseed, rice, wheat, quinoa, buckwheat, barley, oatmeal, cherry pits, or millet seed. The granular filler of other embodiments includes an inorganic material, such as synthetic polymer beads, having an appropriate thermal conductivity.

Alternative embodiments of the thermal exchange material include a malleable homogeneous structure to be contained within the shell 14. The malleable homogeneous structure optionally includes a putty, clay, or thermal gel having the desired thermal conductivity. The thermal gel may be selected from a variety of gel-like or semi-solid liquids that can be used to maintain and disperse heat. The material as described within U.S. Pat. Nos. 5,478,988 and 5,494,598 may be utilized to provide materials that can provide the thermal capabilities of the above-described embodiments. Both U.S. Pat. Nos. 5,478,988 and 5,494,598 are herein incorporated by reference in their entirety to the extent their disclosures do not conflict with this disclosure. The thermal gel of some embodiments includes an elastomeric polymer gel comprising ammonium persulfate, bisacrylamide, acrylamide, water, glycerin, citric acid, and tetramethylethylenediamine (TEMED). By weight, the elastomeric polymer gel includes ingredients in following amounts and forms a gel-like structure having an appropriate thermal conductivity:

TABLE 1

| Material | Percentage by weight (%) |
|---|---|
| Ammonium persulfate | 0.2-0.6 |
| N, N methylene-bisacrylamide | 0.05-0.25 |
| Acrylamide | 15-20 |
| Water | 10-25 |
| Glycerin | 50-75 |
| Citric Acid | 0.01-0.10 |
| TEMED | 0.01-0.10 |

As an illustrative example, the percentage of each ingredient may be as follows:

TABLE 2

| Material | Percentage by weight (%) |
|---|---|
| Ammonium persulfate | 0.41 |
| N, N methylene-bisacrylamide | 0.15 |
| Acrylamide | 17.95 |
| Water | 17.96 |
| Glycerin | 63.44 |
| Citric Acid | .05 |
| TEMED | 4.09 |

The elastomeric polymer gel of some embodiments is formed into a desired shape by injecting substantially equal parts of a solution A and solution B into a preformed mold. Solutions A and B are created by first separating a presolution into a secondary portion and a primary portion. In some embodiments, the secondary portion includes less of the presolution than the primary portion. In other embodiments, the secondary portion includes between approximately 40-50% of the presolution. In certain embodiments, the secondary portion includes between approximately 45-48% of the presolution.

The presolution, itself, includes acrylamide, bisacrylamide, glycerin, citric acid, and water. An acrylamide solution of approximately 50-60% acrylamide and 50-75% of the total water is mixed with the bisacrylamide. After the bisacrylamide is fully dissolved into the acrylamide solution, the glycerin and citric acid may be are added. The glycerin and citric acid are stirred or mixed with the acrylamide-bisacrylamide solution to obtain the resulting presolution. If air bubbles are present in the presolution, the bubbles may be removed either actively or passively (i.e., by keeping the presolution substantially still as the density of the air bubbles forces them to rise from the presolution).

Next, the presolution may be separated into the secondary and primary portions. Solution A is created by adding an ammonium persulfate solution to the secondary portion. The ammonium persulfate solution includes the chosen persulfate amount and the remaining water amount. Each are mixed together before being added to the secondary portion. The ammonium persulfate solution may be prepared either before, during, or after the presolution is prepared. Solution B is created by adding the TEMED to the primary portion and mixing it therein.

Once both Solution A and Solution B are prepared, they may be simultaneously injected into the mold form. Solutions A and B may be injected by multiple discrete syringes, or a dual chamber syringe may be provided. If a dual chamber syringe is utilized, Solutions A and B are drawn into separate chambers using discrete drawing tips. Before injection, a mixing tip is provided and attached to the separate syringe chambers. As the solutions are injected, they will pass from their respective chambers, through a common mixing channel of the mixing tip, and into the mold. Shortly after being injected into the mold, the mixture of solution A and B will harden as an elastomeric polymer gel. After the hardening, the resulting elastomeric polymer gel will be suitable for use as part of the thermal exchange material 16 within the apparatus shell 14.

As discussed above, the thermal exchange material 16 of some embodiments is inserted into the shell 14 through the aperture 22. In alternative embodiments, a separate entry point (not shown) may be provided in the shell 14. The size and shape of the separate entry point may be varied, but should be suitable to receive the thermal exchange material 16. Once insertion of the thermal exchange material 16 is complete, the separate entry point may be permanently or selectively sealed. Optionally, the shell 14 will be formed from one or more discrete pieces. In such embodiments, the thermal exchange material 16 will be placed in or on a first piece of the shell 14 while the remaining shell pieces are joined together around the exchange material 16.

As noted above, some embodiments of the apparatus 10 include a permeable plug 26 that spans the aperture 22. The permeable plug 26 effectively seals the aperture 22 and prevents solid objects from entering or escaping therethrough. Although the plug 26 prevents passage of solid objects, the permeability of the plug 26 (i.e., plug permeability) is sufficient to permit communication of air and moisture. Even after a plug 26 is inserted into the aperture 22, air and moisture may communicate through the aperture 22. Moreover, steam or vapor generated within the inner cavity 18 during use may pass through the permeable plug 26 as it exits the shell 14.

As shown in FIG. 5A-6B, the permeable plug 26 of some embodiments is substantially flush with the shell outer surface 20. In other embodiments, the plug 26 may be positioned such that its top surface (i.e., surface furthest from the inner cavity 18) extends radially above or below the outer surface 20. The plug 26 of some embodiments may be configured to be selectively removable from the shell 14. In such embodiments, the plug 26 may be removed and replaced by a user before or after use. Alternatively, the plug 26 may be permanently disposed in or on the shell 14. If the plug is permanently disposed, a connection formed by adhesive, prongs, or a known mechanical connection maintains the plug 26 in its selected position.

The permeable plug 26, itself, may include one or more breathable fibrous materials. In some embodiments, the fibrous material is cotton, polyester, or hemp. In one embodiment, the fibrous material is a cotton ball. In more embodiments, the plug 26 includes one or more porous, low density foams. In optional embodiments, the permeable plug 26 includes a substantially solid material (e.g., rubber, plastic or metal). Although the solid material, alone, may have an insufficient permeability, the material of such embodiments defines one or more passages suitably sized and configured to permit communication of air and moisture through the plug 26.

Returning to FIG. 1-4, the sleeve 12 is formed to correspond in size and shape with one or more shells 14. Before, or during, use of the apparatus 10, the one or more shells 14 are placed at least partially within the sleeve 12. When the shell 14 is disposed within the sleeve 12, an exterior face 28 of the sleeve 12 is directed radially outward away from the shell 14. Conversely, an interior face 30 is directed radially inward toward the shell 14. In some embodiments, at least one point of the interior face 30 rests against the outer surface 20.

The sleeve 12 also includes one or more vent regions 32. Each vent region 32 allows communication between the ambient environment and the shell 14. If steam is generated within the inner cavity 18, the steam may advantageously pass through the vent region 32 before creating an excess pressure within the sleeve 12. Left unchecked, the steam might otherwise burst through the shell 14 or sleeve 12, damaging the apparatus 10 and potentially harming a user. Air or moisture is permitted to pass through the vent region 32 to the ambient environment outside the enclosed shell 14 and sleeve 12. Some embodiments of the vent region 32 further include a vent hole 34 extending through the sleeve 12. The vent hole 34 is defined between the exterior face 28 and the interior face 30. In other words, the vent hole 34 generally extends along a vent axis 36 through the two faces, thereby providing a direct path for air or moisture to pass through the sleeve 12.

As shown in FIGS. 5A and 6A, some embodiments of the vent hole 34 are positioned in close proximity to an aperture 22. When the shell 14 is disposed within the sleeve 12, the aperture 22 is configured to lie at least partially between the vent hole 34 and the inner cavity 18. As a result, aperture 22 and vent hole 34 provide a fluid path through which air and moisture may pass. This allows communication between the inner cavity 18 and the ambient environment.

Some embodiments include a plurality of apertures 22 and corresponding vent holes 34, as shown in FIG. 6A. In such embodiments, steam and heated air may pass through a first aperture 22A, through a first vent hole 34A, and to the ambient environment. Simultaneously, ambient air will enter the inner cavity 18 through the second vent hole 34B and second aperture 22B.

Figure 3:
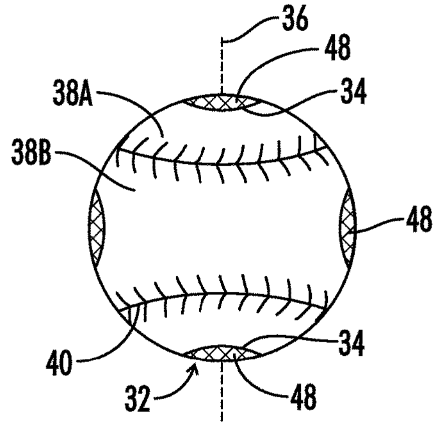
FIG. 3 is a front view of the embodiment of FIG. 1.
Figure 2:
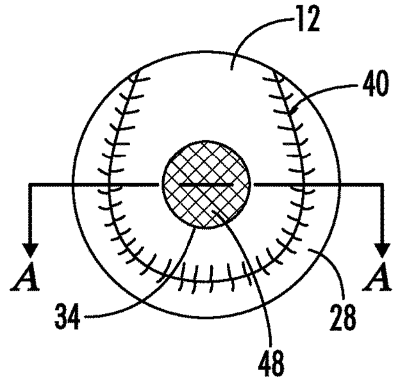
FIG. 2 is an overhead view of the embodiment of FIG. 1.
Figure 4:
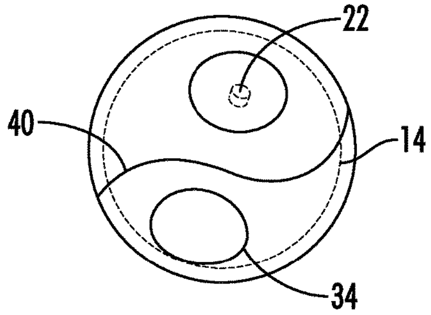
FIG. 4 is a transparent perspective view of a thermal therapeutic apparatus embodiment.
Figure 7A:
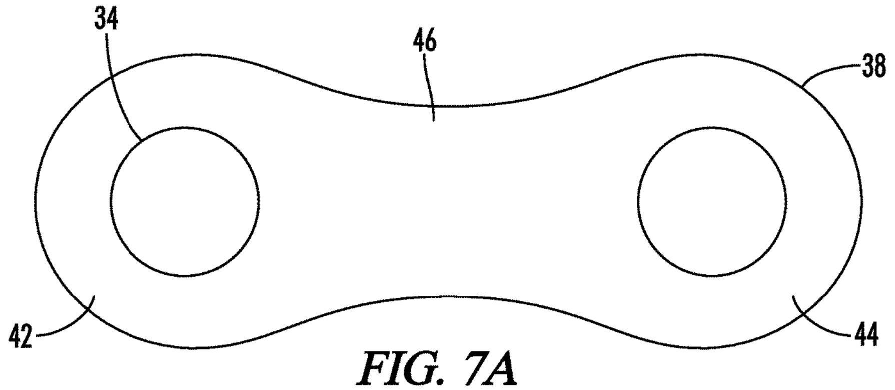
FIG. 7A is a perspective view of an embodiment of a sleeve strip.
Figure 7B:
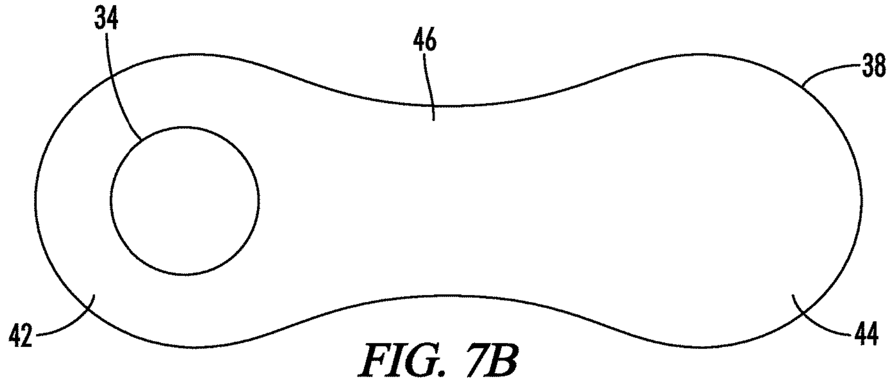
FIG. 7B is a perspective view of another embodiment of a sleeve strip.
Figure 7C:
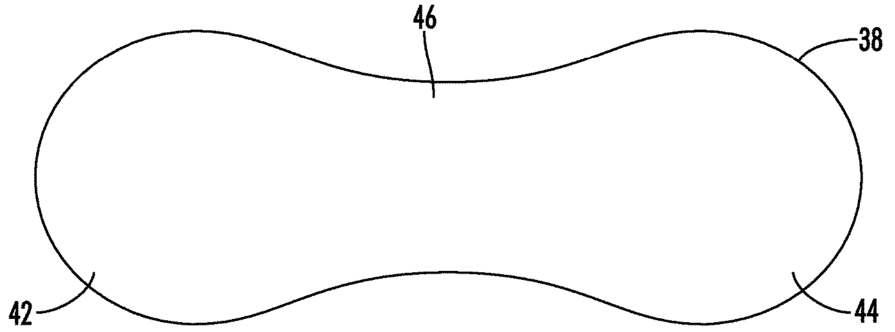
FIG. 7C is a perspective view of yet another embodiment of a sleeve strip.
Figure 8:
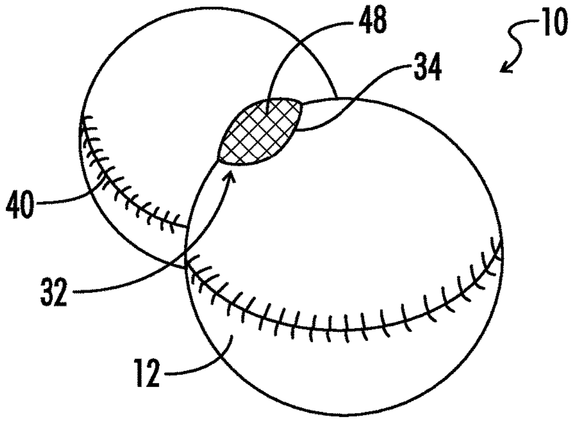
FIG. 8 is a perspective view of a thermal therapeutic apparatus embodiment.
Figure 9:
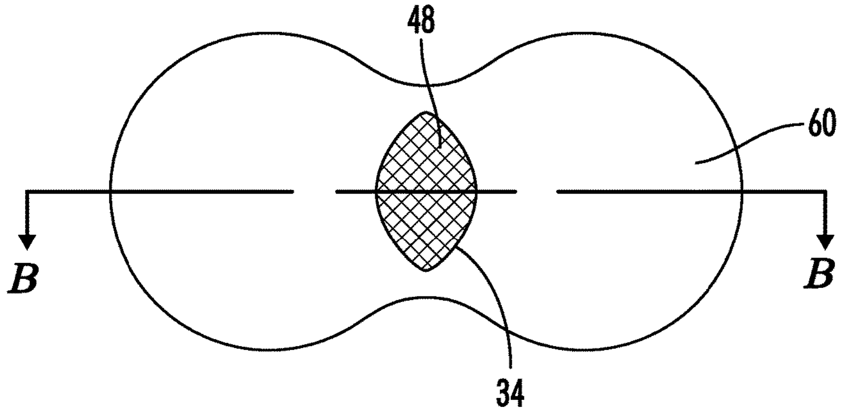
FIG. 9 is an overhead view of the embodiment of FIG. 8.
Figure 10:
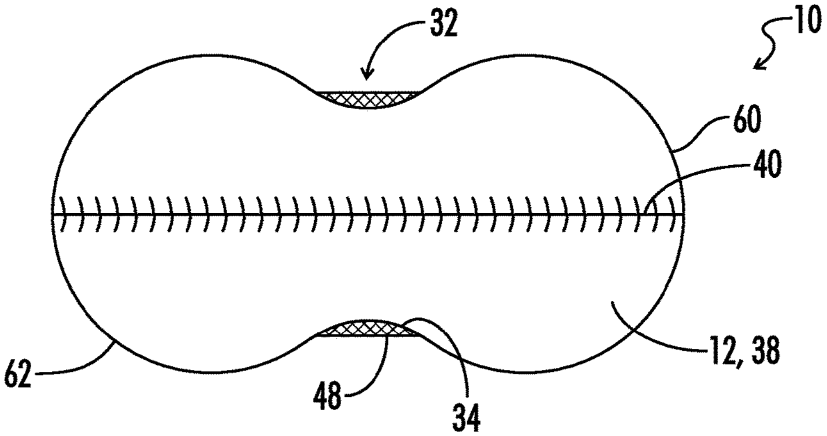
FIG. 10 is a side view of the embodiment of FIG. 8.
Figure 11:
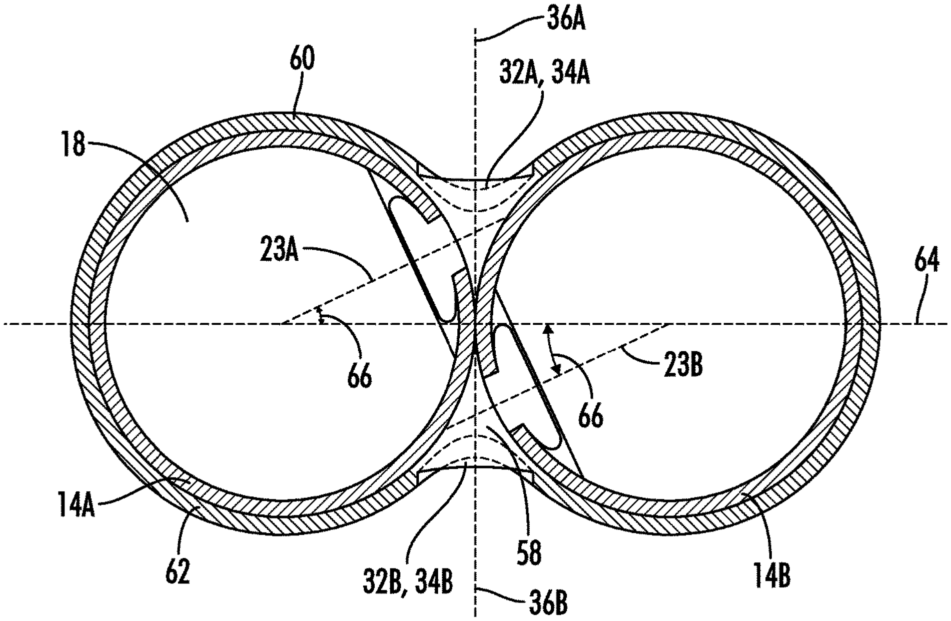
FIG. 11 is a cut-away view along axis B-B of a thermal therapeutic apparatus embodiment.
Figure 12A:
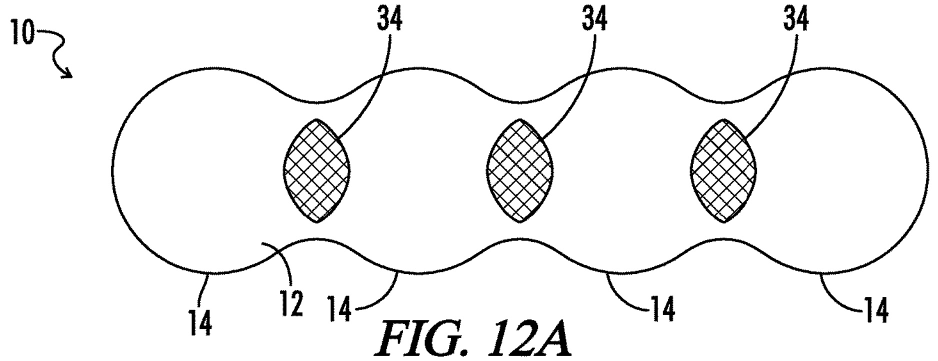
FIG. 12A is an overhead view of a thermal therapeutic apparatus embodiment.
Figure 13A:
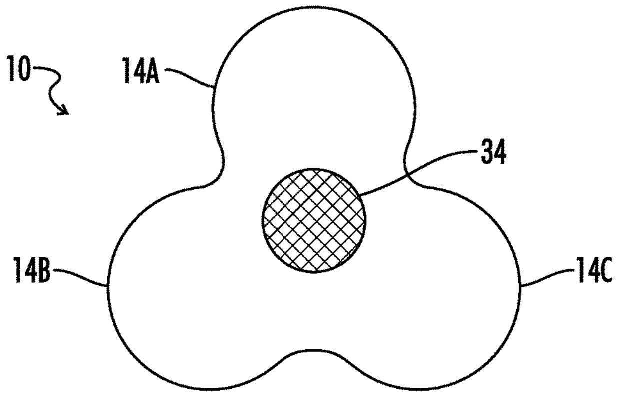
FIG. 13A is a perspective view of a thermal therapeutic apparatus embodiment.
Figure 14A:
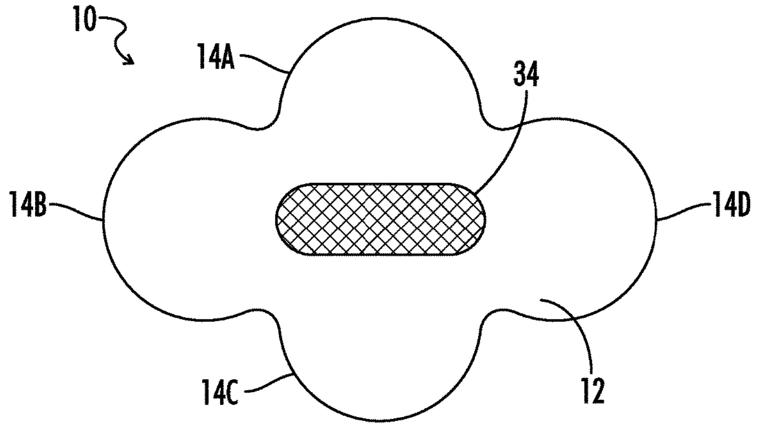
FIG. 14A is an overhead view of a thermal therapeutic apparatus embodiment.
Figure 12B:
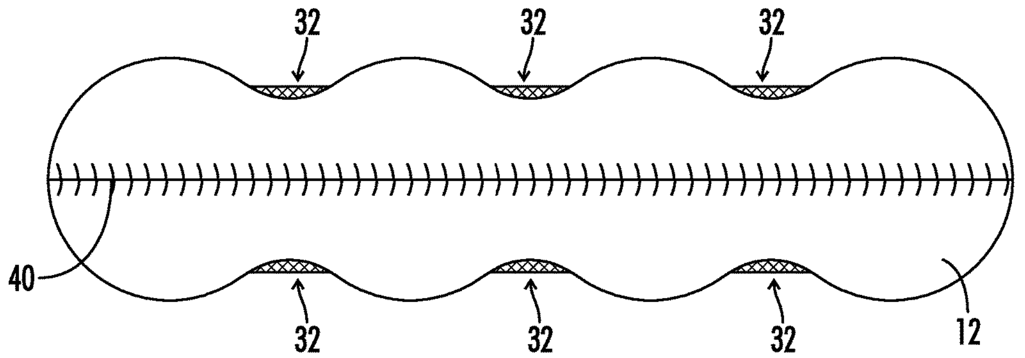
FIG. 12B is a side view of the embodiment of FIG. 12A.
Figure 13B:
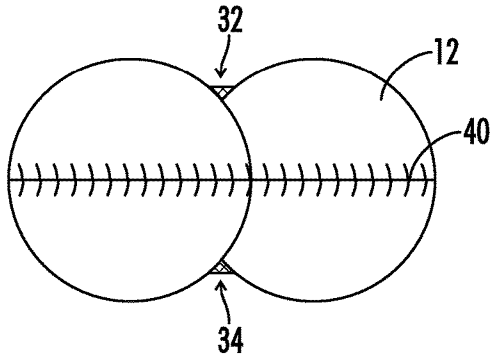
FIG. 13B is a side view of the embodiment of FIG. 13A.
Figure 14B:
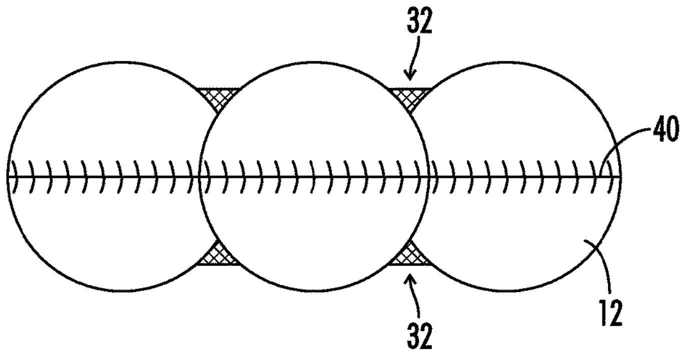
FIG. 14B is a side view of the embodiment of FIG. 14A.
Figure 15A:
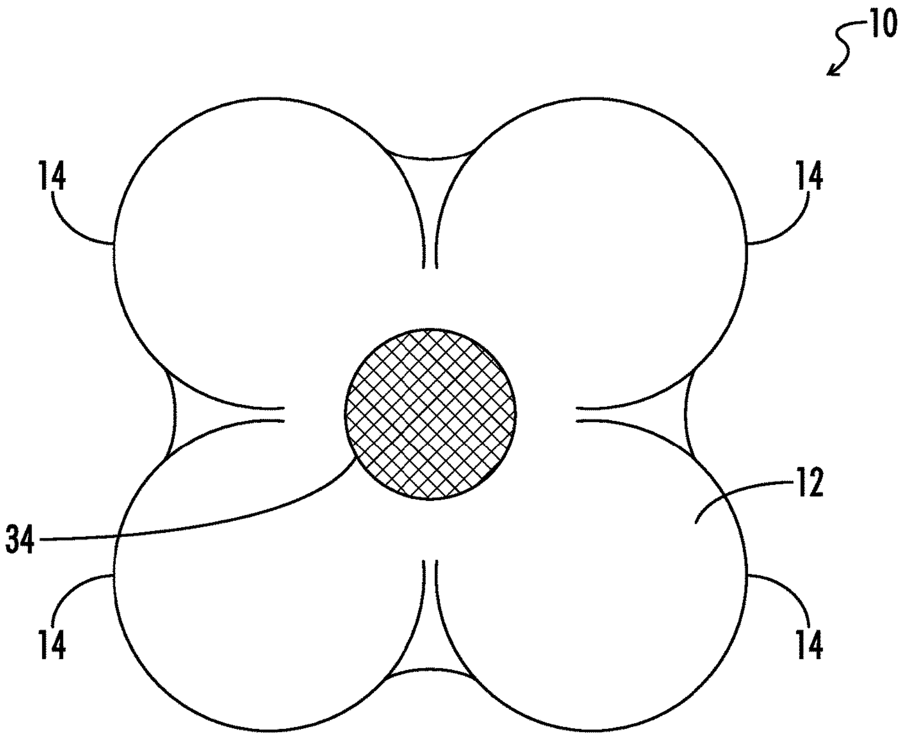
FIG. 15A is an overhead view of a thermal therapeutic apparatus embodiment.
Figure 15B:
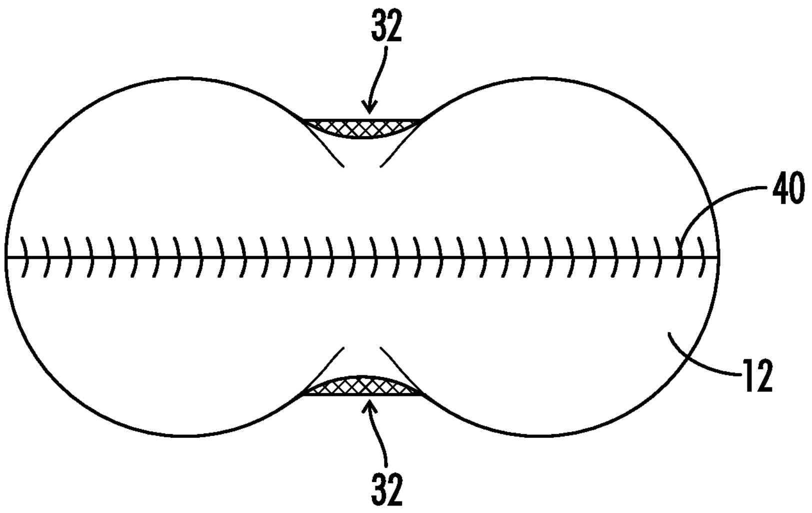
FIG. 15B is a side view of the embodiment of FIG. 15A.
Figure 16:
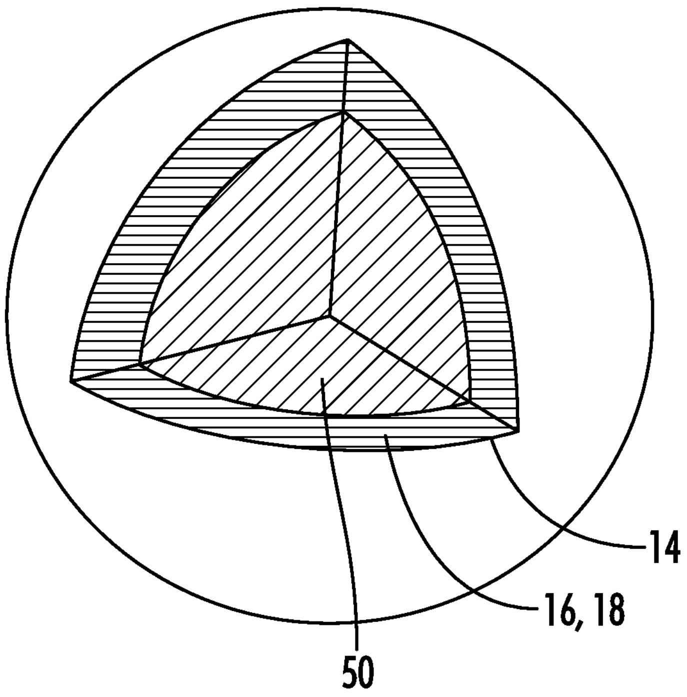
FIG. 16 is a partial-cut-away view of resilient shell embodiment including a rigid core.
Figure 17:
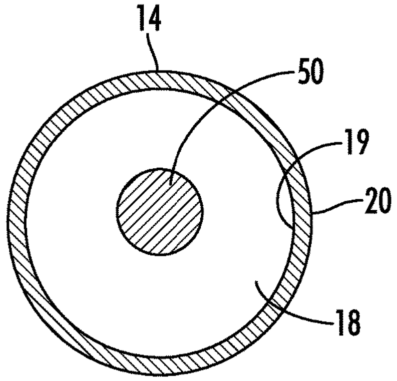
FIG. 17 is a cut-away view of a resilient shell embodiment including a rigid core.

The sleeve 12 of some embodiments includes multiple attached strips 38. As shown in FIG. 1-3, multiple strips 38 may be joined in an interlocking pattern to substantially cover the shell 14 along a seam 40. The interlocking strips 38 each may have a size and shape which corresponds to the shell 14 and to each other. FIG. 7A-7C provides a front view of several strip 38 embodiments in isolation and fully extended as they would appear when laid flat. Each strip includes a first lobed end 42 and a second lobed end 44, as well as a body portion 46 extending between the two ends.

Generally, a vent region 32 may be included at any portion of the strip 38. As illustrated by FIG. 7A, a vent hole 34 may be defined at both the first 42 and second 44 lobed ends. Alternatively, the strip 38 may only define a vent hole at one of the two lobed ends, similar to the strip 38 of FIG. 7B. As another alternative, the strip 38 may not define a vent hole at all. Multiple strip embodiments may be used within a single apparatus 10 to cover the shell 14. For example, one embodiment of the apparatus 10 includes the strip embodiment of FIG. 7B interlocked with the strip embodiment of FIG. 7C. Similarly, another embodiment includes the strip embodiment of FIG. 7A interlocked with the strip embodiment of FIG. 7B. Moreover, some embodiments include two virtually identical strips 38, as shown in FIG. 3.

Multiple strips 38 may attach to each other or to the shell 14 using one or more sleeve fastener. In some embodiments, the sleeve fastener includes an adhesive, hook-and-loop fastener, snap, button, stitching, or another mechanical fastener that is known to one of ordinary skill in the art. A seam 40 forms along the attachment points. Certain embodiments of the seam 40 will be substantially flush with the shell exterior face 28. In other embodiments, the seam 40 will be radially raised or indented with respect to the remaining portion of the sleeve 12. In such embodiments, the amount of increased or decreased radial height may be configured to provide a comfortable texture against a user's skin. In an exemplary embodiment, the seam 40 includes a waterproof blind stitch. Another exemplary embodiment of the seam includes a permeable flat lock stitch.

In some embodiments, the sleeve 12 may be configured to remain substantially fixed with respect to the shell 14 during use. Some embodiments of the sleeve 12 are dimensioned to have a radius or shape approximately equal to the shell 14, thereby creating a tight fit between the sleeve 12 and shell 14. Alternatively, the sleeve 12 has a resting radius or shape which is slightly smaller than the shell 14. In such embodiments, the sleeve 12 elastically deforms to conform to the general shape and size of the shell 14. In optional embodiments, one or more system fastener attaches the sleeve 12 and shell 14. The system fastener of certain embodiments includes an adhesive, button, snap, hook-and-loop fastener, or another mechanical fastener that is known to one of ordinary skill in the art.

The sleeve 12 includes a flexible sleeve material which allows the sleeve to deform during use. The flexible sleeve material of some embodiments includes neoprene, elastane, polyester, cotton, nylon, or elastane. The material may be formed as a continuous, woven, or mesh fabric. Optionally, the sleeve material includes one or more continuous, non-woven sheet of an elastic polymer, plastic, or leather. In some embodiments, the sleeve material is a neoprene mesh fabric between approximately 0.5-10 millimeters thick. In further embodiments, the sleeve material is a neoprene mesh fabric between approximately 1-5 millimeters thick. In certain embodiments, the sleeve material is a neoprene mesh fabric approximately 3 millimeters thick.

Returning to FIG. 1-3, some embodiments of the apparatus 10 include a vent membrane 48 disposed across a portion the vent hole 34. The membrane 48 includes a breathable structure having sufficient permeability to permit communication of air and moisture through the membrane 48. As air and moisture passes to or from the inner cavity 18, the membrane 48 also diffuses the fluid stream. As a result, any steam generated within the shell 14 will be dispersed before passing to the ambient environment.

The membrane 48 of some embodiments substantially covers the entirety of vent hole 34, while other embodiments of the membrane 48 only cover a fraction of the vent hole 34. Certain embodiments of the apparatus 10 include a membrane 48 which substantially covers the shell outer surface 20. In these embodiments, the membrane 48 may form a barrier layer between the shell 14 and sleeve 12. Other embodiments of the apparatus 10 include a membrane 48 which only covers the area of the outer surface 20 not otherwise covered by the vent hole 34. Optionally, the membrane 48 is attached to the sleeve 12. As the sleeve 12 moves in relation to the shell 14, the membrane 48 will also move. The membrane 48 may attach to the sleeve using one or more membrane fastener. The membrane fastener of certain embodiments includes include one or more adhesive, hook-and-loop fastener, snap, button, stitching, or another mechanical fastener that is known to one of ordinary skill in the art. In some embodiments, the membrane 48 is positioned between the sleeve 12 and the shell 14. In other embodiments, the membrane 48 is positioned radially outward from the sleeve 12. In still other embodiments, the membrane 48 is disposed within vent hole 34.

The membrane 48 includes one or more permeable material. In some embodiments, the membrane 48 includes a breathable woven or mesh fabric. In certain embodiments, the membrane includes a cotton, polyester, silk, hemp, elastane, or nylon fabric. In more embodiments, the membrane 48 includes a micro-pique polyester, polyester rib, or nylon mesh fabric.

Figure 18:
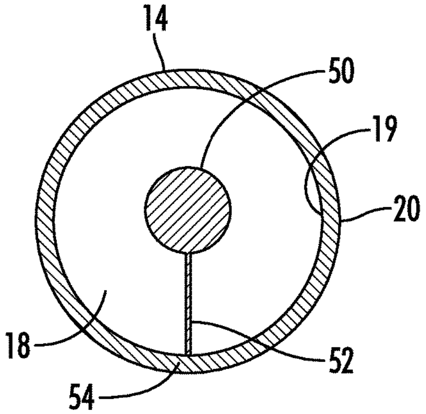
FIG. 18 is a cut-away view of a resilient shell embodiment including a rigid core.
Figure 19:
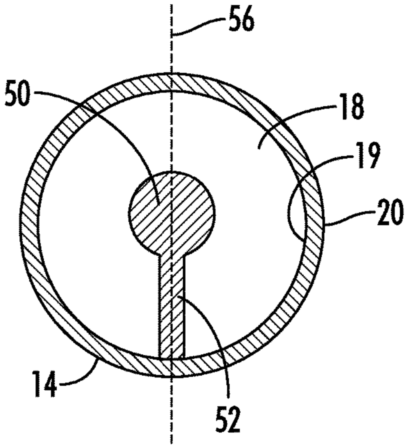
FIG. 19 is a cut-away view of a resilient shell embodiment including a rigid core.
Figure 20:
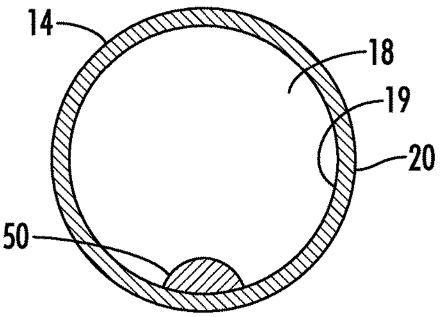
FIG. 20 is a cut-away view of a resilient shell embodiment including a rigid core.

Turning to FIG. 16-20, some embodiments of the apparatus 10 include a rigid core 50 disposed within the shell 14. During use, the rigid core 50 may provide additional resistance in massaging muscles. The thermal exchange material 16 surrounds at least a portion of the rigid core 50. Moreover, the thermal exchange material 16 acts as a resistive barrier between the core 50 and the outer surface 20. In some embodiments, such as that shown in FIG. 17, the core 50 is unattached to the shell 14. Other embodiments include an anchor 52 joined to the core 50 and to the shell wall 24. The anchor 52 thereby maintains the core at position or position range relative to the shell inner cavity surface 19. Advantageously, this position or position range may be maintained as certain embodiments of the thermal exchange material 16 are inserted into the inner cavity 18, preventing the core 50 from moving to an undesired position. FIG. 18 illustrates an anchor 52 including a strand extending radially between the core 50 and a core-cavity attachment point 54. The strand may be flexible or substantially rigid. The embodiment of FIG. 19 includes an anchor axis 56 bisecting the anchor 52, core 50, and shell 14. In FIG. 19, the anchor 52, core 50, and shell 14 are formed as two integral sections which combine along the anchor axis 56. Each section includes a portion of the anchor 52, core 50, and shell 14. When combined, the sections provide a complete anchor 52, core 50, and shell 14.

Although the core 50 is shown as being spherical in shape, other three-dimensional shapes may be utilized without departing from the invention as disclosed.

FIG. 8-15B illustrate several embodiments of the apparatus 10 which include a plurality of resilient shells 14 disposed at least partially within a sleeve 12. In such embodiments, a connection joint 58 is formed in the enclosed area between two adjacent shells 14. A reference plane 64 extends through the connection joint 58 and separates a first side 60 of the sleeve from a second side 62. In some embodiments, the reference plane 64 bisects the first shell 14A and second shell 14B. In other embodiments, the reference axis is parallel to a vent axis 36.

Optionally, one or more vent regions are located above or radially outward from the connection joint 58. As in the embodiment of FIG. 11, some embodiments provide a first vent hole 34A on the first side 60, along with an oppositely-disposed second vent hole 34B on the second side 62. Each vent hole 34 may be included as part of a separate vent region 32A and 32B. In such embodiments, the shells' apertures 22 are positioned away from each other. The first shell aperture 22A is directed toward the first side 60. Air or moisture passing from the first aperture 22A flows through a fluid path and primarily out of the first vent hole 34A. Conversely, the second shell aperture 22B is directed toward the second side 62. Air or moisture passing from that aperture 22B flows through another fluid path and primarily out of the second vent hole 34B. An offset angle 66 is defined between each aperture's axis 23 and the reference plane 64. In some embodiments, each offset angle 66 is between approximately 5-85°. In other embodiments, each angle 66 is between approximately 15-65°. In still more embodiments, each angle 66 is between approximately 20-45°.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention of a new and useful thermal therapeutic apparatus it is not intended that such references be construed as limitations upon the scope of this invention except as set forth in the following claims.

What is claimed is:

1. A thermal therapeutic apparatus comprising:

a first resilient shell having an inner cavity and an outer surface, the shell defining a first aperture extending from the inner cavity to the outer surface with the first aperture having a first aperture axis;

a first thermal exchange material disposed within the inner cavity of the first resilient shell;

a first permeable plug spanning the aperture of the first shell, the first permeable plug having a first plug permeability sufficient to permit passage of air and moisture while preventing passage of the thermal exchange material from the inner cavity of the first shell;

a second resilient shell having an inner cavity and an outer surface, the shell defining an aperture extending from the inner cavity to the outer surface with the second aperture having a second aperture axis;

a second thermal exchange material disposed within the inner cavity of the second resilient shell;

a second permeable plug spanning the aperture of the second shell, the permeable plug having a second plug permeability sufficient to permit passage of air and moisture while preventing passage of the thermal exchange material from the inner cavity of the second shell; and a flexible sleeve at least partially covering the first resilient shell and the second resilient shell, the sleeve including at least one vent region configured to permit communication of air and moisture from within the first shell and second shell through the at least one vent region in the sleeve with the first aperture of the first shell angled toward the second shell and the second aperture of the second shell angled toward the first shell with the first shell in contact with the second shell.

2. The thermal therapeutic apparatus of claim 1, further comprising:

a reference plane bisecting both the first shell and the second shell creating a first side and a second side;

with the first aperture directed toward the first side, and the second aperture directed toward the second side.

3. The thermal therapeutic apparatus of claim 2, wherein the first side includes a first vent region and the second side includes a second vent region.

4. The thermal therapeutic apparatus of claim 2 wherein, the reference plane creates an offset angle between five degrees and eighty-five degrees with the first aperture axis and also with the second aperture axis.

5. The thermal therapeutic apparatus of claim 4, wherein the offset angle is between fifteen degrees and sixty-five degrees with the first aperture axis and also with the second aperture axis.

6. The thermal therapeutic apparatus of claim 4, wherein the offset angle is between twenty degrees and forty-five degrees with the first aperture axis and also with the second aperture axis.

7. The thermal therapeutic apparatus of claim 1, further comprising a vent membrane disposed across a portion of the at least one vent region, the vent membrane having a membrane permeability sufficient to permit communication of air and moisture through the membrane.

8. The thermal therapeutic apparatus of claim 1, further comprising a wherein the first thermal exchange material and the second thermal exchange material including a granular filler disposed within the inner cavity.

9. The thermal therapeutic apparatus of claim 1, further comprising a wherein the first thermal exchange material and the second thermal exchange material includes a malleable homogeneous structure.

10. A thermal therapeutic apparatus comprising:

a first resilient shell having an inner cavity and an outer surface, the shell defining a first aperture extending from the inner cavity to the outer surface with the first aperture having a first aperture axis;

a first thermal exchange material disposed within the inner cavity of the first resilient shell;

a first permeable plug spanning the aperture of the first shell, the first permeable plug having a first plug permeability sufficient to permit passage of air and moisture while preventing passage of the thermal exchange material from the inner cavity of the first shell;

a second resilient shell having an inner cavity and an outer surface, the shell defining an aperture extending from the inner cavity to the outer surface with the second aperture having a second aperture axis;

a second thermal exchange material disposed within the inner cavity of the second resilient shell;

a second permeable plug spanning the aperture of the second shell, the permeable plug having a second plug permeability sufficient to permit passage of air and moisture while preventing passage of the thermal exchange material from the inner cavity of the second shell; and a flexible sleeve at least partially covering the first resilient shell and the second resilient shell, the sleeve including at least one vent region configured to permit communication of air and moisture from within the first shell and second shell through the at least one vent region in the sleeve with the first aperture of the first shell angled toward the second shell and the second aperture of the second shell angled toward the first shell, with at least one of the first and second apertures at least partially spaced from the vent region and with the first shell in contact with the second shell.

* * * * *